US012005044B1

(12) United States Patent
Dou

(10) Patent No.: US 12,005,044 B1
(45) Date of Patent: Jun. 11, 2024

(54) TREATMENT OF AUTISM SPECTRUM DISORDERS WITH ERGOTHIONEINE, SELENONEINE, OR COMBINATIONS THEREOF

(71) Applicant: Autism Therapeutics Inc., Southfield, MI (US)

(72) Inventor: Dexian Dou, Commerce Township, MI (US)

(73) Assignee: Autism Therapeutics Inc., Southfield, MI (US)

( * ) Notice: Subject to any disclaimer, the term of this patent is extended or adjusted under 35 U.S.C. 154(b) by 0 days.

(21) Appl. No.: 18/071,344

(22) Filed: Nov. 29, 2022

(51) Int. Cl.
*A61K 31/4172* (2006.01)
*A61P 25/00* (2006.01)

(52) U.S. Cl.
CPC .......... *A61K 31/4172* (2013.01); *A61P 25/00* (2018.01)

(58) Field of Classification Search
CPC ............................ A61K 31/4172; A61P 25/00
See application file for complete search history.

(56) References Cited

U.S. PATENT DOCUMENTS

| | | | |
|---|---|---|---|
| 2012/0128711 A1 | 5/2012 | Hausman | |
| 2014/0065132 A1 | 3/2014 | Hsiao et al. | |
| 2014/0121156 A1 | 5/2014 | Hausman | |
| 2014/0363379 A1 | 12/2014 | Hausman | |
| 2015/0157648 A1 | 6/2015 | Hausman | |
| 2019/0358274 A1 | 11/2019 | Adams | |
| 2021/0369676 A1 | 12/2021 | Samant | |

FOREIGN PATENT DOCUMENTS

| | | | |
|---|---|---|---|
| WO | 2005116657 A2 | 12/2005 | |
| WO | 2017/181158 A1 | 10/2017 | |
| WO | WO-2020231906 A1 * | 11/2020 | ............. A23L 33/10 |
| WO | 2021/158601 A1 | 8/2021 | |

OTHER PUBLICATIONS

Yamashita, World J. Biol. Chem., vol. 1(5), pp. 144-150, publ. 2010 (Year: 2010).*
Pamela E. Ventola, Agreement Among Four Diagnostic Instruments for Autism Spectrum Disorders in Toddlers, Aug. 1, 2006.
Dirk Grundemann, Discovery of the Ergothioneine Transporter, Feb. 23, 2005.
Noritaka Nakamichi, Ergothioneine and Central Nervous System Disease, Mar. 23, 2022.
Takahiro Ishimoto, Ergothioneine in the Brain, Nov. 22, 2001.
Takahiro Ishimoto, Ergothioneine-Induced Neuronal Differentiation is Mediated Through Activation of S6K1 and Neurotrophin 4/5-TrkB Signatling in Murine Neural Stem Cells, Jul. 20, 2018.
Yoshiki Matsuda, Ergothioneine, A Metabolite of the Gut Bacterium *Lactobacillus reuteri*, Protects Against Stress-Induced Sleep Disturbances, May 28, 2020.
Hyungju Park, Neurotrophin Regulation of Neural Circuit Development and Function, Jan. 2013.
Eric J. Huang, Neurotrophins: Roles in Neuronal Development and Function, Oct. 6, 2009.
Monica Segura, Neurotrophin Blood-Based Gene Expression and Social Cognition Analysis in Patients with Autism Spectrum Disorder, Oct. 16, 2014.
Yumiko Tamashita, Discovery of the Strong Antioxidant Selenoneine in Tuna and Selenium Redox Metabolism, May 26, 2010.
Khouloud El Hanafi, First Time Identfication of Selenoneine in Seabirds and its Potential Role in Mercury Detoxification, Nov. 26, 2022.
Junko Masuda, Dietary Supplementation of Selenoneine-Containing Tuna Dark Muscle Extract Effectively Reduces Pathology of Experimental Colorectal Cancers in Mice, Sep. 27, 2018.
Takayuki Teruya, Whole-Blood Metabolomics of Dementia Patients Reveal Classes of Disease-Linked Metabolites, May 14, 2021.
Noritaka Nakamichi, Oral Administration of the Food-Derived Hydrophilic Antioxidant Ergothioneine Enhances Object Recognition Memory in Mice, Sep. 13, 2019.
Mamoru Fukuch, Aminothioneine, A Product Dervived from Golden Oyster Mushrooms (*Pleurotus cornucopiae* var. *citrinopileatus*), Activates $Ca^{2+}$ Signal-Mediated Brain-Derived Neurotrophic Factor Expression in Cultured Crotical Neurons, Oct. 11, 2021.
Yuanyuan Shen, Non-Invasive, Targeted, and Non-Viral Ultrasound-Mediated Brain-Derived Neurotrophic Factor Plasmid Delivery for Treatment of Autism in a Rat Model, Sep. 1, 2022.
Isabel Baron-Mendoza, Changes in the No. and Morphology of Dendritic Spines in the Hippocampus and Prefrontal Cortex of the C58/J Mouse Model of Autism, Sep. 20, 2021.
Hiroshi Kondoh, Decline of Ergothioneine in Frailty and Cognition Impairment, Feb. 3, 2022.
Barry Halliwell, Ergothioneine—A Diet-Derived Antioxidant with Therapeutic Potential, Jun. 15, 2018.
John B. Vincent, Genetic Linkage Analysis of the X Chromosome in Autism, with Emphasis on the Fragile X Region, 2005.
Martine Lamy, Pharmacological Management of Behavioral Disturbances in Children and Adolescents with Autism Spectrum Disorders, Aug. 2015.
Michiaki Yamashita, Identification and Determination of Selenoneine, 2-Selenyl-Na, Na, Na-Trimethyl-L-Histidine, as the Major Organic Selenium in Blood Cells in a Fish-Eating Population on Remote Japanese Islands, Nov. 8, 2013.
Ann Hematol (2012) Original Article "N-acetylcysteine reduces oxidative stress in sickle cell patients", Dated Feb. 10, 2012.
European Journal of Pharmaceutical Sciences Article (2020) "Pharmacokinetic profile of N-acetylcysteine amide and its main metabolite in mice using new analytical method".
HHS Public Access Author Manuscript (2016) "Advancing the understanding of autism disease mechanisms through genetics".

(Continued)

*Primary Examiner* — Sarah Pihonak
(74) *Attorney, Agent, or Firm* — The Dobrusin Law Firm, PC

(57) ABSTRACT

A method of treatment of autism spectrum disorders comprising ergothioneine (ET), selenoneine (SeET), or combinations thereof. The methods may include the use of edible compositions comprising ergothioneine (ET), selenoneine (SeET), or combinations thereof.

20 Claims, 2 Drawing Sheets

(56) References Cited

OTHER PUBLICATIONS

PCT International Search Report & Written Opinion dated Feb. 8, 2024, Application No. PCT/US2023/079492.
Matsuda Yoshiki et al: "ergothioneine, a Metabolite of the gut bacterium *Lactobacillus reuteri*, protects agains stress-induced sleep disturbances", Translation Psychiatry, May 28, 2020, p. 170.

* cited by examiner

TREATMENT OF AUTISM SPECTRUM DISORDERS WITH ERGOTHIONEINE, SELENONEINE, OR COMBINATIONS THEREOF

FIELD

The present teachings relate to the treatment of autism spectrum disorders with ergothioneine and/or its analog selenoneine.

BACKGROUND

Autism, or autism spectrum disorders (ASD), refers to a broad range of developmental neurologic disorders commonly appearing in early developmental stages. ASD individuals have various clinical manifestations mainly in social communication and interaction with others, and restricted or repetitive behaviors or interests. Other behavioral disorders in speaking, learning, and movement are also observed in impacted individual.

Diagnosis of ASD is mostly behaviorally based. Since there is no one-size-fits-all approach to diagnose ASD, several diagnostic methods are currently adopted in clinical practice. The only clinical approved method to treat ASD core behaviors is behavioral analysis (BA). There are so far no FDA approved drugs to target core behaviors involved in ASD. It would therefore be desirable to have an effective and safe treatment for ASD core behaviors.

The prevalence of ASD creates a critical therapeutic need. Numerous therapeutic methods are intensively explored. There are over 800 clinical studies performed or ongoing for the alleviation of ASD and associated disorders in the United States. Effective treatment drugs are significantly lacking as no medications have been available to treat or alleviate ASD core phenotypes.

United States Patent Publication No. US 2014/0065132 describes ergothioneine as an ASD-related metabolite and addresses treatments to adjust gut microbiota that will modify the levels of wide variety of ASD-related metabolites.

International Patent Publication No. WO 2021/158601 discloses the treatment of a variety of health conditions with ergothioneine by modifying telomere length. However, dosage and nature of treatment for ASD is not addressed.

International Patent Publication No. WO 2017/181158A1 describes improvement of at least one symptom of a social behavior deficit using probiotic therapies for developmental disorders and other neurological disorders.

It would therefore be beneficial to have specific treatment protocols for ASD using dietary supplements. The teachings herein are directed to methods for the use of dietary ergothioneine and selenoneine to treat ASD and alleviate ASD associated behavioral disorders.

SUMMARY

The present teachings relate to a method of treatment of autism spectrum disorders comprising administering a therapeutically effective amount of ergothioneine (ET), selenoneine (SeET), or combinations thereof to a human subject. The ergothioneine (ET), selenoneine (SeET), or combinations thereof may be administered in the form of powders, tablets, capsules, drinks, or other edible forms.

The ergothioneine (ET), selenoneine (SeET), or combinations thereof may be administered in a dosage range of from about 0.45 µg to about 800 mg/kg body weight (bw) per day. The ergothioneine (ET), selenoneine (SeET), or combinations thereof may be administered in a dosage range of from about 0.01 to about 17,600 mg daily. The ergothioneine (ET), selenoneine (SeET), or combinations thereof may be administered in a dosage range of from about 1 µg to about 300 mg/kg body weight (bw) per day. The ergothioneine (ET), selenoneine (SeET), or combinations thereof may be administered in a dosage range of from about 0.07 to about 12,000 mg daily. The ergothioneine (ET), selenoneine (SeET), or combinations thereof may be administered in a dosage range of from about 0.1 to about 75 mg/kg body weight (bw) per day. The ergothioneine (ET), selenoneine (SeET), or combinations thereof may be administered in a dosage range of from about 1 to about 1000 mg daily. The ergothioneine (ET), selenoneine (SeET), or combinations thereof may be administered in a dosage range of from about 0.5 to about 20 mg/kg body weight (bw) per day.

The administration may occur between a single time and daily for a period of 70 years. The administration may occur daily for a period of at least three months. The administration may occur daily for a period of at least six months. The administration may occur daily for a period of at least one year. The administration may occur daily for a period of at least five years.

The method may include administering ergothioneine (ET) in a dosage range of from about 0.2 to about 20 mg/kg body weight (bw) per day. The method may include administering ergothioneine (ET) in a dosage range of from about 1 to about 5 mg/kg body weight (bw) per day. The method may include administering ergothioneine (ET) in a dosage range of from about 10 to about 1000 mg per day. The method may include administering ergothioneine (ET) in a dosage range of from about 20 to about 500 mg per day. The method may include administering ergothioneine (ET) in a dosage range of 20 mg per day or more. The method may include administering ergothioneine (ET) in a dosage range of 35 mg per day or more. The method may include administering ergothioneine (ET) in a dosage range of 40 mg per day or more. The method may include administering ergothioneine (ET) in a dosage range of 50 mg per day or more.

A CARS-2 score of the human subject may be reduced by at least 2. A CARS-2 score of the human subject may be reduced by at least 5.

The teachings herein may be further directed to a method of treatment of autism spectrum disorders comprising administering a therapeutically effective amount of ergothioneine (ET), selenoneine (SeET), or combinations thereof to a human subject, wherein the therapeutically effective amount of ergothioneine (ET), selenoneine (SeET), or combinations thereof is administered in a dosage range of from about 0.45 µg to about 800 mg/kg body weight (bw) per day, and wherein a CARS-2 score of the human subject is reduced by at least 5.

DETAILED DESCRIPTION

Figure 1:
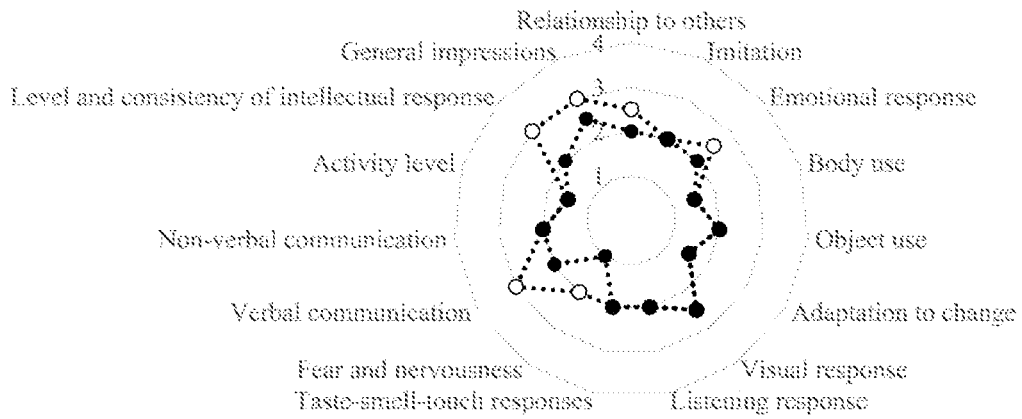
FIG. 1 is a graph showing CARS-2 value changes after treatment relating to Example 1.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Ergothioneine (ET) was discovered in 1909 and named after the ergot fungus (*Claviceps purpurea*) from where it was first purified. The chemical structure of ET was later determined, showing to be an analog of histidine amino acid. ET is found in various microorganisms, especially abundant in edible mushrooms. For example, the porcini mushroom (*Boletus edulis*), may contain ET as much as 181 mg/100 g dry weight.

Selenoneine (SeET) is a close analog of ET where sulfur is substituted by selenium (as shown in their structures below). SeET was firstly discovered from tuna where it is showed to be abundant in tuna muscle.

Structures of ergothioneine (ET), selenoneine (SeET) and histidine are depicted below. ET (with a molecular weight of 229.3 Dalton) and SeET (with a molecular weight of 275.2 Dalton) are both plus-charged trimethyl-betaine derivatives of histidine. ET is a metabolite synthesized in microorganisms from histidine precursor.

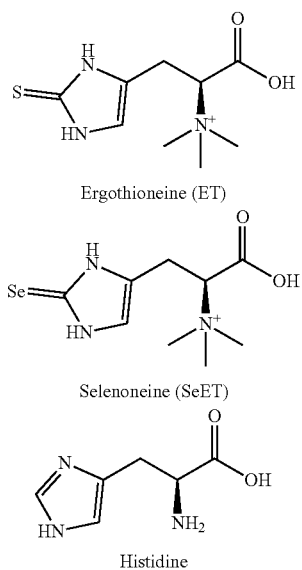

Ergothioneine (ET)

Selenoneine (SeET)

Histidine

In general, ET has been known to be a strong anti-oxidation and anti-inflammation agent. It was also discovered to promote neurogenesis. Similar to ET, SeET is also found to have antioxidation activities. In addition, SeET was found to detoxify mercury in marine animal and fish-eating populations. Studies in human subjects showed that ET has anti-aging function. A reverse association of ET with cognitive decrease was also discovered in clinical metabolomics studies. Results showed that ET is significantly decreased in various cognition-related disorders, such as mild cognitive impairment and frailty. Clinically, dietary ET supplements improved stress-induced sleep disturbance.

ASD diagnosis has increased dramatically in recent decades. Currently, ASD incidence is approximately 1 in 44 or 2.27% of children in the United States. It is also a common disorder world-wide. ASD includes a wide range of behavioral manifestations, usually diagnosed from early developmental stages. The ASD behaviors relate to social skills and communication, repetitive behaviors, and language skills. Those disorders can be mild, moderate, or severe, and the signs and symptoms are different in each individual.

The four major diagnostic systems based on behavioral manifestations are: 1) CARS-2 (Childhood Autism Rating Scale, Second Edition); 2) DSM-IV (Diagnostic and Statistical Manual of Mental Disorders, Fourth Edition); 3) ABC (Autism Behavior Checklist); and 4) ADOS-2 (Autism Diagnostic Observation Schedule, Second Edition). Each of these methods has its specific application. Among them, CARS-2 was showed to have several advantages. In terms of sensitivity and specificity, the criterion validity of CARS-2 showed better sensitivity (with a sensitivity score of 0.86) than DSM-IV (with a sensitivity score of 0.71), and a better specificity (with a specificity score of 0.79) versus DSM-IV (with a specificity score of 0.75). ABC diagnostic method lacks specificity in distinguishing ASD from other types of developmental disorders, with a higher rate of false negatives (46%), while the false negative rate of using CARS-2 is 0%. In the comparison of CARS-2 and ADOS-2, clinical judgment agreed with each other, but CARS-2 is a simpler and less expensive tool for autism assessment. Overall, CARS-2 showed to be a reliable and well-adopted method for autism evaluation and diagnosis.

Specific causes for ASD remain unknown. Both genetic and environmental factors may be involved in ASD progresses. The most well-known genetic linked ASD is Fragile X-ASD, where the mutation happens in X chromosome.

Accompanying disorders are also common in ASD-affected individuals, such as gut microbiota dysbiosis (gut dysbiosis) and poor gut function, lowered capacity to detoxify neurotoxin and heavy metals, and increased oxidative stress and inflammation. However, these types of accompanying disorders and their association with core behavioral disorders are not well established.

Behavioral treatments remain the mainstay of treatment for the core symptoms of ASD including communication deficits, social interaction deficits and repetitive behavior. Medications for ASD core behaviors are not available. Currently there are only two FDA-approved drugs (Risperidone and Aripiprazole) for the treatment of irritability associated with ASD in children. Anti-seizure medication and drugs to treat co-occurring conditions that often appear with ASD are also prescribed to target those specific symptoms.

ASDs are disorders with abnormal synaptic function, connectivity, and neurogenesis. Neurotrophins are essential neuro growth factors regulating neurogenesis, including the development, maintenance, and function of nervous systems. Therefore, their functionalities are critical for normal brain physiology and as a result, alternation of their expression is associated with complicated neurological disorders including ASD. The promotion of neurogenesis is considered to be an effective therapeutic strategy for several neuropsychiatric disorders.

Four structural-related mammal neurotrophins have been identified, named NGF (nerve growth factor), BDNF (brain-derived neurotrophic factor), NT-3 (neurotrophin-3), and NT-4/5 (neurotrophin-4/5). All of them are critically required for neuron differentiation, survival, and function. Neurotrophin NT-3 and NT-4/5 induce differentiation of spinal and basal forebrain cholinergic neurons, as well as hippocampal neurons. It plays a positive role in helping the survival of cultured embryonic dopaminergic neurons. Neurotrophin NT-3 and NT-4/5 can also transiently support the survival of trigeminal and jugular neurons during embryonic development.

There is rising evidence about the potentially significant role of neurotrophin in ASD. Preliminary studies found that NT3 and NT4/5 were downregulated in ASD compared with controlled populations. Therefore, promoting neurotrophin expression could possibly help to maintain synaptic plasticity and alleviate ASD symptoms.

ET can permeate the blood-brain barrier using its unique transporter system, OCTN (coded by SLC22A4). ET was found to significantly upregulate neurotrophin NT-3 and NT-4/5, suggesting its therapeutic potential for neurological disorders through promoting neurotrophin levels. Studies in animals also showed that orally ingested ET promotes neurogenesis in the hippocampal dentate gyrus, increases the neural stem cells (NSCs) population, and exerts antidepressant-like effects.

The potentials of ET in alleviating neurological diseases were reported. In human population, ET levels in serum were found to be reversely associated with multiple neurodegenerative conditions including dementia, Alzheimer's deteriorating cognitive ability. ET was also claimed to protect against degenerative retinal damage, Parkinson's Disease, and Alzheimer's Disease (Identification methods for ergothioneine transporter modulators and therapeutic uses thereof. D. Grundemann, E. Schomig. U.S. Pat. No. 8,492,106 B2).

Based upon the potential functions of ET, the teachings herein propose the use of ET and SeET for ASD treatment. ET can promote neurogenesis, likely through upregulating neural growth factors such as BDNF. In addition to its direct regulation of CNS, ET can also protect neuron damage induced by elevated oxidative stress and inflammations.

Examples are described below for using ET to treat ASD-affected individuals. Each of the four individuals identified in the examples has various severity of ASD. The examples set forth herein are directed to the use of ET dietary supplement for a period of three months. Each individual showed significantly improved ASD manifestations with reduced scores as evaluated by CARS-2.

SeET is a structural analog of ET with selenium (Se) replacing sulfur (S) on the imidazole ring. It is theoretically a stronger antioxidant with the standard reducing potential of −0.49V (E$^{o'}$−0.49V) while that of ET is −0.06V (E$^{o'}$−0.06V). Previous studies showed SeET as having strong antioxidant and anti-inflammation activity and a detoxifying function against heavy metal toxicity in fish. The biosynthesis of SeET and its biological functions are similar to that of ET. SeET can also pass across the blood-brain barrier. As a result, SeET and ET may share similar functions in the treatment of ASD and related neurological diseases.

ET is naturally occurring and exists in a large variety of food. Mushrooms are known to contain the highest concentration of ET. Gut microbes can also synthesize ET. Animal studies showed that social defeat stress increased growth of gut microbes such as *Lactobacillus reuteri*, in turn, in correlation with increased ET levels synthesized by *L. reuteri*. Fecal transplantation of ET-producing *L. reuteri* was proposed to improve gut function.

The European Food Safety Authority (EFSA) in 2016 approved the use of ET as a food additive and supplement including for pregnant women and infants. The United States Food and Drug Administration (FDA) granted ET the status of "Generally Recognized as Safe" (GRAS) to be used as a food additive and supplement in 2017 (GRAS Notice #734 for ergothioneine. 2017; 1-209). Therefore, ET can be safety and regularly used as dietary supplement.

EFSA Panel approved ET dosage at 2.82 mg/kg body weight (bw) per day for infants, 3.39 mg/kg bw per day for toddlers, and 1.31 mg/kg bw per day for adults including pregnant and breastfeeding women. The maximum allowed ET dosage is as high as 800 mg/kg bw per day based on the no-observed-adverse-effect level (NOAEL). The examples below adopted ET dosages of 1 and 2 mg/kg bw per day for a continuous three month period to treat ASD individuals, which are within the dosage approved by EFSA. ET was purchased from manufacturers, the FDA-certified Generally Recognized as Safe (GRAS) product.

SeET was discovered in tuna in Japan. SeET is the major selenium compound in fish muscles, and fish is an important source of selenium in the fish-eating population. Many island countries have long understood and taken advantage of the health benefits of foods containing SeET. As a result, SeET is understood as safe for human beings. SeET therefore is deemed as a food ingredient.

The use of dietary supplements of ET and SeET for ASD treatment has certain advantages. They are both food-origin compounds and they may both have general function to promote neurogenesis and to reduce oxidative stress and inflammation. They can also both be supplied regularly as dietary supplements.

Among multiple available diagnostic approaches, the CARS-2 scoring system shows to be a sensitive and specific method, which evaluates comprehensive psychological and behavioral conditions. The examples below therefore adopted the CARS-2 system to evaluate ET treatment effects in four ASD individuals.

To obtain a CARS-2 score, each individual is rated on a scale of 1 (normal) to 4 (severely abnormal) with respect to each of the 15 criteria ("relationship to others", "imitation", "emotional response", "body use", "object use", "adaptation to change", "visual response", "listening response", "taste-smell-touch responses", "fear and nervousness", "verbal communication", "non-verbal communication", "activity level", "level and reliability of intellectual responses", and "general impressions"). A total score is obtained by combining all of 15 separate scores, ranging from 15 to 60. A score of 15 is normal. Scores below 30 are considered very mild or non-autistic; 30-36.5 are considered mild to moderate ASD and scores greater than 36.5 are considered severe ASD. The scoring can be provided by either primary care giver or the parents. The treatment results are summarized below.

Example 1—Application of ET to Treat an 8-Year-Old Girl with ASD

An 8-year-old girl weighing 27 kg was diagnosed with ASD at 4 years-old.

Method of treatment: ET (2 mg/kg bw per day, 54 mg daily) powder is dissolved in drinking water (200 mL). The individual is treated by ET for three months. ET has no color, no taste when dissolved in water.

Results: CARS-2 scores before and after ET treatment are provided. In each category, scores 1-4 are given, as shown in Table 1. This individual shows higher levels in "verbal communication" and "level and consistency of intellectual response". In general, she receives a score of 33, which represent mild ASD.

After treatment, scores of "fear and nervousness", "verbal communication", "level and reliability of intellectual responses", and "general impressions", are significantly improved (Table 1). "Relationship to others" is slightly improved. There are no major changes to observe in other categories. The total score is reduced to 28.5 (after treatment from 33 (before treatment). A visual representation of the score results is shown in FIG. 1.

TABLE 1

| The CARS-2 categories of behaviors | Before treatment | After treatment |
| --- | --- | --- |
| Relationship to others | 2.5 | 2 |
| Imitation | 2 | 2 |
| Emotional response | 2.5 | 2 |
| Body use | 1.5 | 1.5 |
| Object use | 2 | 2 |
| Adaptation to change | 1.5 | 1.5 |
| Visual response | 2.5 | 2.5 |
| Listening response | 2 | 2 |
| Taste-smell-touch responses | 2 | 2 |
| Fear and nervousness | 2 | 1 |
| Verbal communication | 3 | 2 |
| Non-verbal communication | 2 | 2 |
| Activity level | 1.5 | 1.5 |
| Level and consistency of intellectual response | 3 | 2 |
| General impressions | 3 | 2.5 |
| Total scores | 33 | 28.5 |

Example 2—Application of ET to Treat a 5-Year-Old Girl with ASD

A 5-year-old girl weighing 21 kg was diagnosed with ASD at the age of 4.

Method of treatment: ET (2 mg/kg bw per day, 42 mg daily) powder is dissolved in drinking water (200 mL). The individual is treated by ET for three months.

Results: CARS-2 scores before and after ET treatment are provided. In each category, scores 1-4 are given, as shown in Table 2. This individual shows high levels in "relationship to others", "verbal communication", "non-verbal communication", and "activity level". She receives a score of 32, which represent mild ASD.

Figure 2:
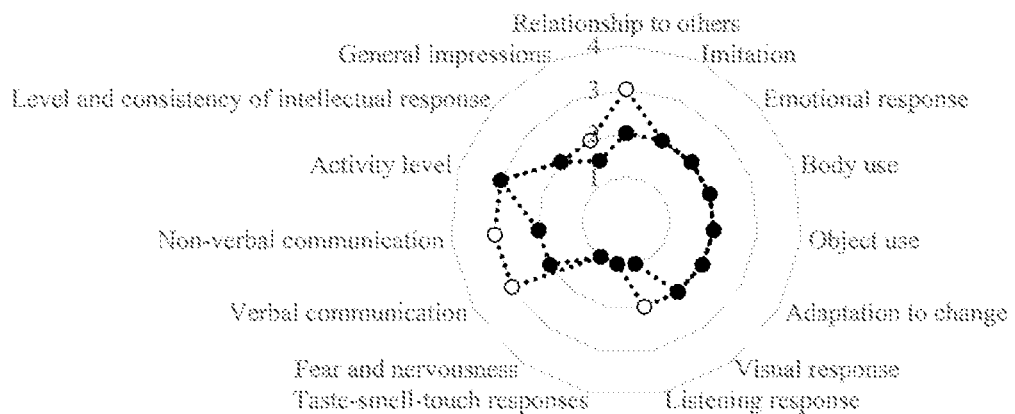
FIG. 2 is a graph showing CARS-2 value changes after treatment relating to Example 2.

After treatment, scores of "relationship to others", "verbal communication" "non-verbal communication", and "listening response", are significantly improved (Table 2, FIG. 2). There are no major changes observed in other categories. Total score is reduced to 27.5 after treatment from 33 (before treatment). A visual representation of the score results is shown in FIG. 2.

TABLE 2

| The CARS-2 categories of behaviors | Before treatment | After treatment |
| --- | --- | --- |
| Relationship to others | 3 | 2 |
| Imitation | 2 | 2 |
| Emotional response | 2 | 2 |
| Body use | 2 | 2 |
| Object use | 2 | 2 |
| Adaptation to change | 2 | 2 |
| Visual response | 2 | 2 |
| Listening response | 2 | 1 |

TABLE 2-continued

| The CARS-2 categories of behaviors | Before treatment | After treatment |
| --- | --- | --- |
| Taste-smell-touch responses | 1 | 1 |
| Fear and nervousness | 1 | 1 |
| Verbal communication | 3 | 2 |
| Non-verbal communication | 3 | 2 |
| Activity level | 3 | 3 |
| Level and consistency of intellectual response | 2 | 2 |
| General impressions | 2 | 1.5 |
| Total scores | 32 | 27.5 |

Example 3—Application of ET to Treat a 5-Year-Old Boy Diagnosed with ASD and Asperger's Syndrome A 5-year-old boy weighing 22 kg was diagnosed with Asperger's Syndrome at the age of 3. Today Asperger's syndrome is technically no longer a diagnosis on its own. It is now part of a broader category of ASD.

Method of treatment: ET (2 mg/kg bw per day, 42 mg daily) powder is dissolved in drinking water (200 mL). The individual is treated by ET for three months.

Results: CARS-2 scores before and after ET treatment are provided. In each category, scores 1-4 are given, as shown in Table 3. He receives a score of 20.5, which represent minor ASD.

Figure 3:
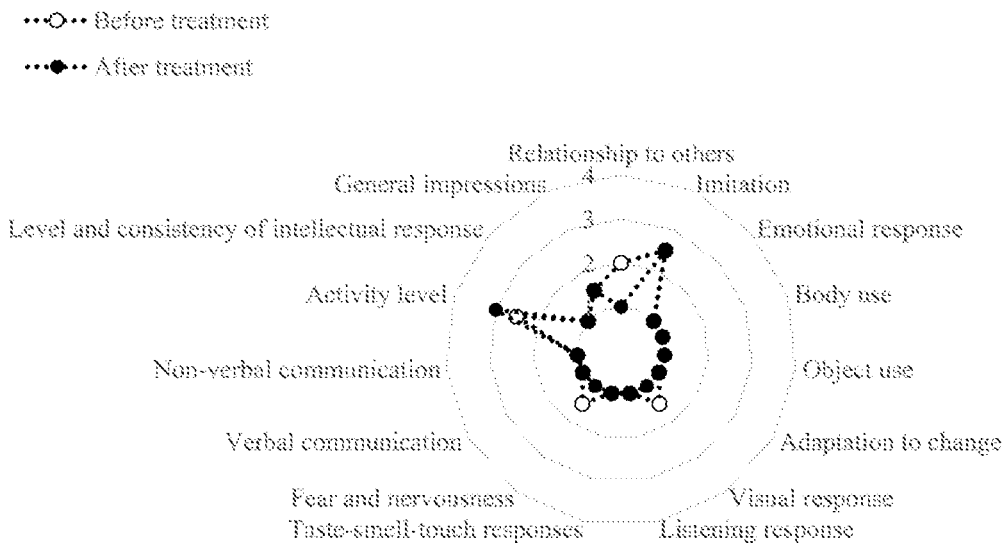
FIG. 3 is a graph showing CARS-2 value changes after treatment relating to Example 3.

After treatment, scores of "relating to others" are significantly improved (Table 3, FIG. 3). The "relating to others", "visual response" and "visual response", tend to be normal (scores of 1). Total score is reduced to 19 after treatment from 20.5 (before treatment). A visual representation of the score results is shown in FIG. 3.

The diagnosis after ET treatment is no longer ASD, and more likely a mild Attention-Deficit/Hyperactivity Disorder (ADHD). ADHD is one of the most common neurodevelopmental disorders of childhood. ASD and ADHD overlap in some criteria such as emotional response, dysregulation, and hyperfocus. An estimated 30 to 80 percent of children with autism also meet the criteria for ADHD and, conversely, 20 to 50 percent of children with ADHD for autism.

TABLE 3

| The CARS-2 categories of behaviors | Before treatment | After treatment |
| --- | --- | --- |
| Relationship to others | 2 | 1 |
| Imitation | 2.5 | 2.5 |
| Emotional response | 1 | 1 |
| Body use | 1 | 1 |
| Object use | 1 | 1 |
| Adaptation to change | 1 | 1 |
| Visual response | 1.5 | 1 |
| Listening response | 1 | 1 |
| Taste-smell-touch responses | 1 | 1 |
| Fear and nervousness | 1.5 | 1 |
| Verbal communication | 1 | 1 |
| Non-verbal communication | 1 | 1 |
| Activity level | 2.5 | 3 |
| Level and consistency of intellectual response | 1 | 1 |
| General impressions | 1.5 | 1.5 |
| Total scores | 20.5 | 19 |

Example 4—Application of ET to Treat a 32-Year-Old Man with ASD

A 32-year-old man weighing 74 kg was diagnosed with ASD at the age of 4.

Method of treatment: ET (1 mg/kg bw per day, 74 mg daily) powder is dissolved in drinking water (200 mL). The individual is treated by ET for three months.

Results: CARS-2 scores before and after ET treatment are provided. In each category, scores 1-4 are given, as shown in Table 4. This individual shows higher levels in "imitation", "object use", "listening response", "taste-smell-touch responses", "verbal communication", "activity level", "level and reliability of intellectual responses". In general, he receives a score of 37.5, which represent severe ASD.

Figure 4:
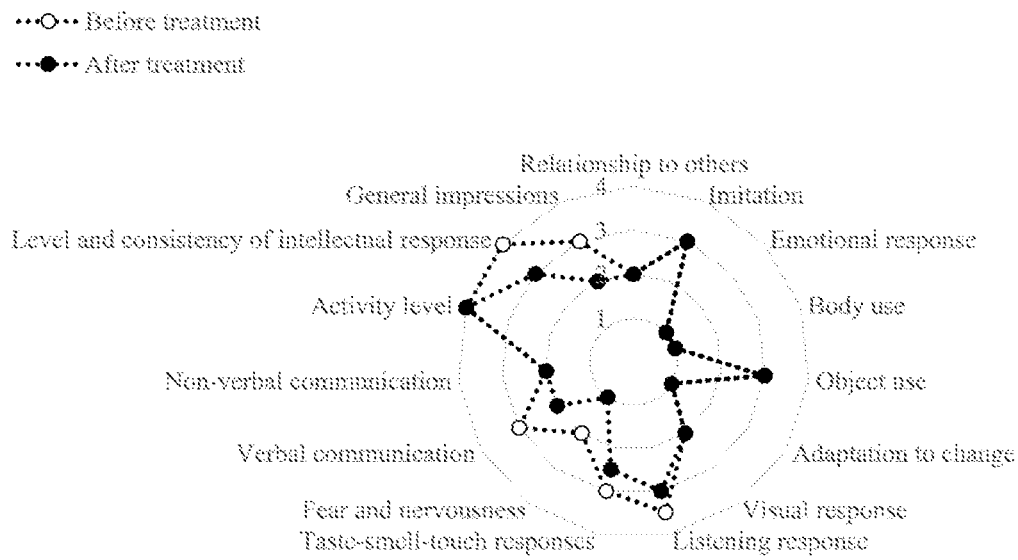
FIG. 4 is a graph showing CARS-2 value changes after treatment relating to Example 4.

After treatment, scores of "listening response", "taste-smell-touch response", "fear and nervousness", "verbal communication", and "level and reliability of intellectual responses", are significantly improved (Table 4, FIG. 4). The total score is reduced to 31.5 (mild ASD) after treatment from 37.5 (severe ASD before treatment). A visual representation of the score results is shown in FIG. 4.

TABLE 4

| The CARS-2 categories of behaviors | Before treatment | After treatment |
|---|---|---|
| Relationship to others | 2 | 2 |
| Imitation | 3 | 3 |
| Emotional response | 1 | 1 |
| Body use | 1 | 1 |
| Object use | 3 | 3 |
| Adaptation to change | 1 | 1 |
| Visual response | 2 | 2 |
| Listening response | 3.5 | 3 |
| Taste-smell-touch responses | 3 | 2.5 |
| Fear and nervousness | 2 | 1 |
| Verbal communication | 3 | 2 |
| Non-verbal communication | 2 | 2 |
| Activity level | 4 | 4 |
| Level and consistency of intellectual response | 4 | 3 |
| General impressions | 3 | 2 |
| Total scores | 37.5 | 31.5 |

In examples 1-4, the average of total CARS-2 score are decreased from 30.75 to 26.62 with statistical significance (T=4.37, P=0.022 by paired student t-test). The categories that show significance are: "relationship to others" (T=2.61, P=0.079); "fears and nervousness" (T=2.61, P=0.079); "verbal communication (T=7.00, P=0.006); and "overall impression" (T=1.44, P=0.09). The results show good treatment effects of ASD by ET.

The teachings herein are directed to application of ET and SeET to treat ASD by alleviating ASD behaviors and co-occurring conditions such as gut dysfunction, sleeping disorders, anxiety, communication, verbal and movement, and the like. In addition, this study tested effects of ET in four individuals who are diagnosed with ASD at various severity. Results showed that ET dietary supplement at 1 and 2 mg/kg bw per day, for example, can significantly improve ASD behavioral scores (CARS-2). ET in accordance with the teachings herein regarding dosing can be used as a therapeutic agent for ASD management and treatment. Based on the safety doses of ET specified by EFSA as a dietary supplement, the range is set within 0.1-800 mg/kg bw per day or 2-17,600 mg daily. A close ET analog, SeET, will also have comparable therapeutic effects, which will function as a neurogenesis substance. The applications of ET and SeET for ASD treatment represent a novel and safe therapeutic strategy via using nutritional supplements.

The methods or compositions provided herein may include a purified ET or purified SeET. The purified ET or SeET may be a natural form of purified ergothioneine. The purified ergothioneine may have purity of about 98% or greater. The ET may comprise L-ergothioneine.

The dosing may vary depending upon whether ergothioneine (ET) alone is selected, selenoneine (SeET) alone is selected, or the two are combined. Generally, regardless of which supplement is selected, the supplement may be administered in a dosage range of from about 0.45 µg to about 800 mg/kg body weight (bw) per day. The ergothioneine (ET), selenoneine (SeET), or combinations thereof may be administered in a dosage range of from about 0.01 to about 17,600 mg daily.

In the event that ET alone is utilized, ET may be administered in an amount of 0.01 to about 800 mg/kg body weight (bw) per day. ET may be administered in an amount of 0.01 to about 0.2 mg/kg body weight (bw) per day. ET may be administered in an amount of 0.2 to about 2 mg/kg body weight (bw) per day. ET may be administered in an amount of 2 to about 50 mg/kg body weight (bw) per day. ET may be administered in an amount of 50 to about 800 mg/kg body weight (bw) per day. ET may be administered in an amount of at least 0.01 mg/kg body weight (bw) per day. ET may be administered in an amount of at least 0.2 mg/kg body weight (bw) per day. ET may be administered in an amount of at least 2 mg/kg body weight (bw) per day. ET may be administered in an amount of at least 50 mg/kg body weight (bw) per day. ET may be administered in a dosage range of 20 mg per day or more. ET may be administered in a dosage range of 35 mg per day or more. ET may be administered in a dosage range of 40 mg per day or more. ET may be administered in a dosage range of 50 mg per day or more.

In the event that SeET alone is utilized, SeET may be administered in an amount of 1 µg to about 1 mg/kg body weight (bw) per day. SeET may be administered in an amount of 1 mg to about 10 mg/kg body weight (bw) per day. SeET may be administered in an amount of at least 1 µg/kg body weight (bw) per day. SeET may be administered in an amount of at least 1 mg/kg body weight (bw) per day. SeET may be administered in an amount of at least 10 mg/kg body weight (bw) per day. SeET may be administered in a dosage range of 0.01 mg per day or more. SeET may be administered in a dosage range of 0.1 mg per day or more. SeET may be administered in a dosage range of 1 mg per day or more. SeET may be administered in a dosage range of 10 mg per day or more.

The length of treatment may vary depending upon patient age, disease severity, prevalent symptoms and other factors that are known to vary amongst individuals with ASD. The length of the supplement administration may occur between a single time and daily for a period of 70 years. The administration occurs daily for a period of at least three months. The administration occurs daily for a period of at least six months. The administration occurs daily for a period of at least one year. The administration occurs daily for a period of at least five years.

Any of the test protocols used to determine the presence of ASD may observe improved results when the treatments described herein are utilized. Specifically, CARS-2, DSM-IV, ABC and ADOS-2 protocols may all improve as a result of the treatments described herein. More specifically, CARS-2 scores may be reduced by at least 2, at least 5, or even at least 10.

The methods described herein may be free of any fecal transplant processes. The methods described herein may be free of any infusion processes. The methods described herein may be free of any process requiring directly contacting cells or any body organ with the ET, SeET, or combination thereof. The methods described herein may be free of any incubation process. The methods described herein may be free of any blood test to determine levels of ET or SeET. The methods described herein may be free of the administration of any additional supplement, excipient, or other active ingredient.

The methods described herein may comprise administering a therapeutically effective amount of a supplement consisting essentially of ergothioneine (ET), selenoneine (SeET), or combinations thereof to a human subject. The methods described herein may comprise administering a therapeutically effective amount of a supplement consisting essentially of ergothioneine (ET) to a human subject. The methods described herein may comprise administering a therapeutically effective amount of a supplement consisting essentially of selenoneine (SeET) to a human subject.

As used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the comparative teaching of amounts expressed as weight/volume percent for two or more ingredients also encompasses relative weight proportions of the two or more ingredients to each other, even if not expressly stated. For example, if a teaching recites 2% A, and 5% B, then the teaching also encompasses a weight ratio of A:B of 2:5. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of (namely, the presence of any additional elements, ingredients, components or steps, does not materially affect the properties and/or benefits derived from the teachings; or even consist of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A method of treatment of autism spectrum disorders comprising:
   administering a therapeutically effective amount of ergothioneine (ET) without other active ingredients in a dosage range of from about 0.1 to about 75 mg/kg body weight (bw) per day for at least one month to a human subject;
   wherein a CARS 2 score of the human subject is reduced by at least one point.

2. The method of claim 1, wherein the ergothioneine (ET) is administered in the form of powders, tablets, capsules, drinks, or other edible forms.

3. The method of claim 2, wherein the ergothioneine (ET) is administered in a dosage range of from about 0.01 to about 17,600 mg daily.

4. The method of claim 1, wherein the ergothioneine (ET) is administered in a dosage range of from about 0.07 to about 12,000 mg daily.

5. The method of claim 2, wherein the ergothioneine (ET) is administered in a dosage range of from about 1 to about 1000 mg daily.

6. The method of claim 2, wherein the administration occurs daily for a period of at least three months.

7. The method of claim 1, wherein the administration occurs daily for a period of at least six months.

8. The method of claim 1, wherein the administration occurs daily for a period of at least one year, or even at least 5 years.

9. The method of claim 1, comprising administering ergothioneine (ET) in a dosage range of from about 0.2 to about 20 mg/kg body weight (bw) per day.

10. The method of claim 2, comprising administering ergothioneine (ET) in a dosage range of from about 1 to about 5 mg/kg body weight (bw) per day.

11. The method of claim 6, comprising administering ergothioneine (ET) in a dosage range of from about 10 to about 1000 mg per day.

12. The method of claim 1, comprising administering ergothioneine (ET) in a dosage range of from about 20 to about 500 mg per day.

13. The method of claim 1, wherein the CARS-2 score of the human subject is reduced by at least 2, or even at least 5.

14. The method of claim 1, include administering ergothioneine (ET) in a dosage range of 20 mg per day or more, 35 mg per day or more, 40 mg per day or more, or 50 mg per day or more.

15. A method of treatment of autism spectrum disorders comprising administering a therapeutically effective amount of ergothioneine (ET) and optionally selenoneine (SeET) to a human subject;
   wherein the therapeutically effective amount of ergothioneine (ET) and optionally selenoneine (SeET)-is administered in a dosage range of from about 0.45 µg to about 800 mg/kg body weight (bw) per day; and
   wherein a CARS-2 score of the human subject is reduced by at least 1.5.

16. The method of claim 15, wherein the administration occurs daily for a period of at least three months.

17. The method of claim 15, wherein the administration occurs daily for a period of at least six months.

18. The method of claim 15, wherein the administration occurs daily for a period of at least one year, or even at least 5 years.

19. The method of claim 15, wherein the CARS-2 score of the human subject is reduced by at least 2.

20. The method of claim 15, wherein the CARS-2 score of the human subject is reduced by at least 5.

* * * * *